United States Patent
Bair

[11] 3,940,752
[45] Feb. 24, 1976

[54] TRANSDUCING SYSTEM
[76] Inventor: Willard E. Bair, 405 Sunnycrest Court West, Urbana, Ill. 61801
[22] Filed: Feb. 26, 1974
[21] Appl. No.: 446,052

[52] U.S. Cl.............. 340/189 M; 340/182; 340/206
[51] Int. Cl.² ............................................. G08C 19/16
[58] Field of Search ........... 340/206, 189 M, 188 R, 340/182, 200, 189 R

[56] References Cited
UNITED STATES PATENTS

| | | | |
|---|---|---|---|
| 2,468,703 | 4/1949 | Hammel | 340/206 |
| 3,582,921 | 6/1971 | Krieger | 340/189 M |
| 3,641,536 | 2/1972 | Prosprich | 340/206 |
| 3,742,472 | 6/1973 | Bryant | 340/206 |

Primary Examiner—Thomas B. Habecker
Attorney, Agent, or Firm—Daniel M. Rosen

[57] ABSTRACT

A transducer sytem comprising a plurality of patient mounted transmitters, each of the transmitters including means for generating an asymmetric wave or a variable periodic pulse train, the asymmetry or variable periodicity of said pulse train being proportional to the quantity being transduced, each of said transmitters including an output electrode. A receiver is also provided including portable hand held input electrode electrostatically coupled to one of the transmitter electrodes, the receiver including means for converting the variable periodicity or asymmetry to a magnitude representative of the transduced quantity in proportion to the variable periodicity or asymmetry.

22 Claims, 11 Drawing Figures

TRANSDUCING SYSTEM

This invention relates to sensing systems and more particularly to sensing transmitter and receiver systems for use in sensing measurements from locations removed from the transmitter.

The conventional format for utilizing pluralities of remote transducers including remote transmitting devices for cooperation with a single receiver employs radio frequency transmission and the employment of varying frequency signals indicative of a varying parameter. One conventional form of parameter transduced is that of temperature measurement. In environments wherein many transducing transmitters operate in continuous operation within relatively close proximity, it is extremely difficult for a receiver unit to distinguish between the various signals emitted from the various transducers. In addition, the use of varying frequency to indicate varying parameters must of necessity, utilize a receiver capable of receiving the frequency range transmitted. Thus, it is necessary to repeatedly tune the receiver to insure that the frequency of transmission will coincide with the frequency being detected. In an environment utilizing pluralities of transmitters, it is often necessary, in order to prevent overlap of transmitted signals, to require each of the transmitters to transmit over a different frequency range, thereby necessitating either a plurality of receivers or a single receiver which must be tuned to receive each individual transmission frequency. In addition, the relatively higher current drain of conventional transmitters results in requiring larger battery supplies or reduced battery life, thereby making the utilization of such units in an environment requiring miniaturization and portability difficult. In an environment such as the medical field, utilization of a portable low current transmitter of relatively small size which may be attached to the body from which the temperature is to be transduced and transmitted is thus greatly desirable.

It is therefore the prime object of the present invention to provide a transducing system employing a transmitter and receiver having wireless communication and which does not rely on radio frequency transmission.

It is a further object of the present invention to provide a plurality of transducer transmitters cooperating with a single receiver which does not require individual adjustment of the receiver for each transmitter and which will be able to distinguish between each transmitted signal.

The foregoing objects are accomplished by employing electrostatic or capacitive coupling between the transmitter and receiver, and to communicate information therebetween by means of an asymmetric square wave or an aperiodic pulse train. By choosing the frequency of the pulse train to be relatively low, within the audio range as opposed to the radio range, a single receiver may be utilized to read the signals from a selected transmitter without the necessity of frequency adjustment by the receiver operator.

The advantages of the foregoing arrangement over a conventional transducer transmitter receiver system are evident, particularly in the area of medical instrumentation. By employing a thermally sensitive transducer-transmitter, having a relatively low current draw, a relatively small electronic circuit may be designed to be attached by means of suitable adhesive on a suitable temperature transducing area of a patient. The receiver may then be employed as a small portable battery powered unit which a nurse or attendant will carry to the bedside to monitor the output of a patient's transmitter. Thus, the nurse or attendant can determine the patient's temperature without disturbing the patient. In addition, the transducer transmitter may be placed in continuous operation when the patient is admitted to the hospital so that the nurse or attendant may determine the patient's temperature as desired without the undue waiting time necessitated by conventional mercury thermometer techniques. Clinical as well as economical desirability is therefore evident.

The foregoing objects and brief description of the present invention will become more apparent from the following more detailed description and appended drawings wherein

FIGS. 3A – E illustrate the waveforms generated in accordance with the circuits of FIGS. 2A, 2B and 2C;

FIGS. 5A – E illustrate waveforms generated in accordance with the receivers shown in FIGS. 4A and 4B;

Figure 1:
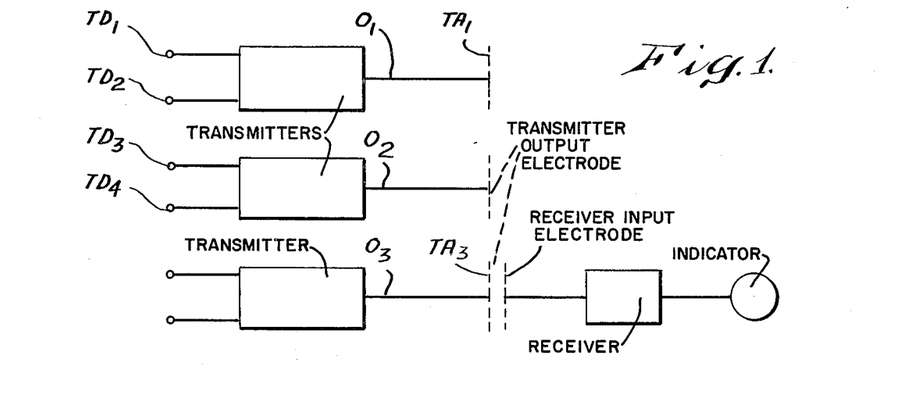
FIG. 1 is a block diagram of a transducer transmitter-receiver system illustrating the utilization of the present invention.

Referring now to FIG. 1, the transducer-transmitter-receiver system utilized in accordance with the present invention is illustrated. As shown therein, a plurality of transmitters indicated generally as $T_1$, $T_2$ $T_3$, etc., are each provided with a plurality of transducer inputs indicated generally as $TD_1$, $TD_2$, etc. For temperature measurement, the transducers may be temperature sensitive components such as resistors or capacitors and which are located in proximity to a body, the temperature of which is to be measured. The transduced signals are converted into an electrical representation within each of the transmitters and applied along the output lines 01, 02 and 03 to the respective output electrodes which may be designated as electrodes $TA_1$, $TA_2$ $TA_3$ for purposes of description, and so on. A receiver unit R is provided with a receiver electrode also designated for descriptive purposes as an input electrode RA and an output indicator I. When it is desired to detect the output of any of the operating transmitters, the receiver input electrode RA is placed into proximity with the desired one of the transmitter output electrodes $TA_1$, $TA_2$, $TA_1$, etc.

In environments such as medical instrumentations, particularly for use within a hospital, it is particularly desirable for all of the transmitters to be identical so that a single detecting instrument may be used to observe the temperature of all patients under the surveillance of an attendant. In this situation, as in other situations requiring similar criteria of measurement, it becomes necessary to limit the range of transmission to avoid interference from adjacent transmitter units. It has been discovered that this can be accomplished by electrostatic or capacitive coupling between the transmitter and receiver at low frequency rather than radio frequency. The use of the capacitive coupling electrodes permits a reliable and wireless form of transmission with a relatively low interference pattern, operating merely by placing the receiver input electrode in close proximity to the transmitter output electrode. In addition, the use of such a system allows all of the transmitters to be continuously operative, thereby obviating the need for individual activation when a reading is desired.

Figure 2A:
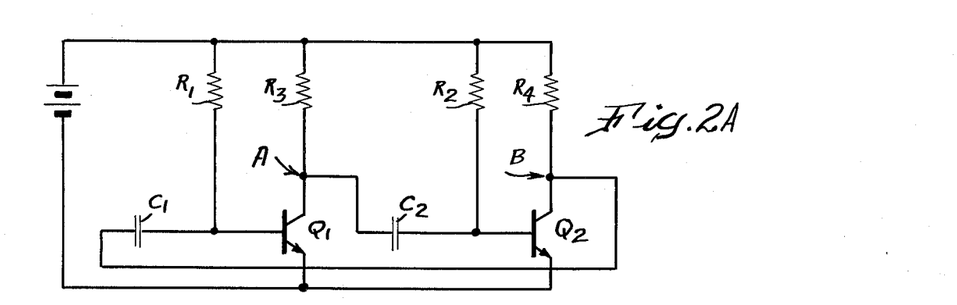
FIG. 2A is a circuit diagram of a multivibrator utilizing temperature dependent components for asymmetry.
Figure 2B:
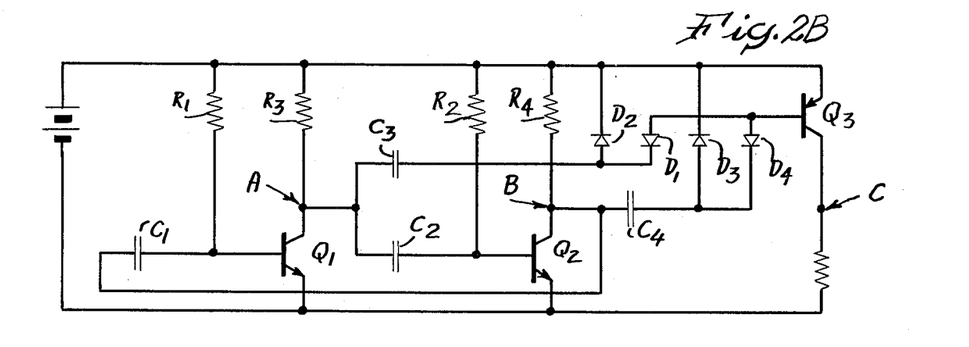
FIG. 2B is a modification resulting in a variable periodic pulse train providing an asymmetric waveform.
Figure 2C:
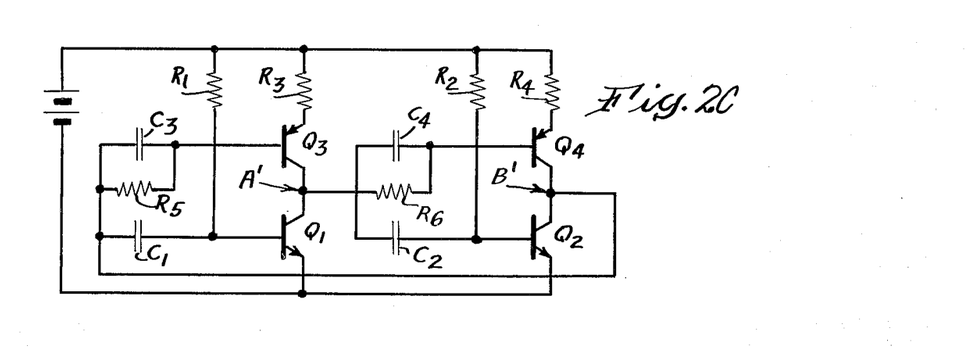
FIG. 2C is a preferred form of multivibrator utilized in accordance with the invention to provide a waveform suitable for direct coupling to the antenna and with the added advantage of relatively low power consumption.

With reference now to FIG. 2, various transmitter devices will be explained to illustrate the operation of the present invention.

Figure 3:
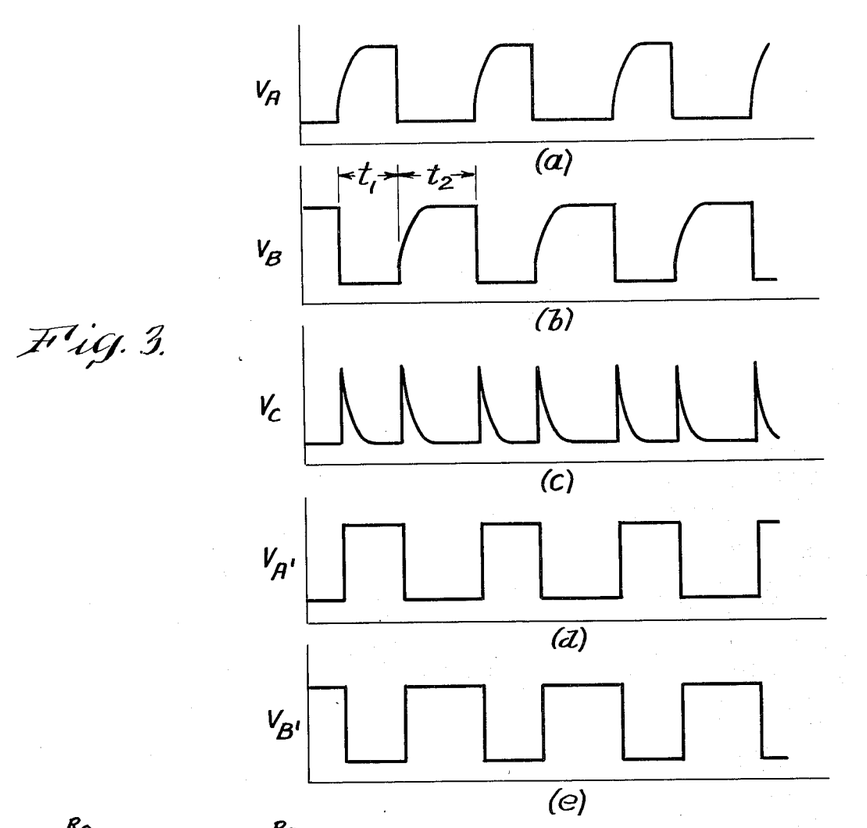

As shown in FIG. 2A, a basic temperature sensing electronic circuit is illustrated. The circuit constitutes a standard multivibrator for which outputs at points A and B are shown in the graphical relationships of FIGS. 3A and 3B. In this circuit, the time interval $t_1$ shown in FIG. 3A and 3B is determined by and is proportional to the product $R_1C_1$ and the interval $t_2$ by $R_2C_2$. The resistors $R_3$ and $R_4$ provide biasing to the alternating on and off switches represented by transistors $Q_1$ and $Q_2$. The operation of the multivibrator is straight forward and need not be set forth herein. By using temperature sensitive resistors and capacitors, the times $t_1$ and $t_2$ may thus be made temperature dependent. It will be evident that the temperature dependent frequency of the output of the circuit may be measured by any conventional frequency detecting system. However, a disadvantage of using frequency measurement as the basis of reception lies in the fact that the frequency generated by a multivibrator in free running form is dependent upon the voltage applied to the entire circuit. In addition, for a battery powered operation over a period of normal hospitalization or, for inaccessible or other remote use, a change in supply voltage due to battery drain would necessarily have to be overcome to provide satisfactory performance. Thus, if the resistor $R_1$ is selected to have a temperature coefficient differing from the temperature coefficient of $R_2$, the ratio of the intervals of $t_1$ and $t_2$ will be temperature dependent but independent of the supply voltage. Stated in another way, although the frequency of the waveform generated by the multivibrator illustrated in FIG. 2A will vary should the voltage vary, the ratio of the intervals $t_1$ and $t_2$ will not vary in accordance with supply voltage but only with temperature. Alternatively, it is possible to use capacitors such as $C_1$ and $C_2$ having different temperature coefficients with the same results. In addition, a combination of different coefficients for both resistors and capacitors is also possible and offers the greatest sensitivity in the resulting indication.

The capacitive coupling between transmitter and receiver requires a rise and fall rate occurring at the transitions of the multivibrator which must be relatively large in order to provide adequate coupling across the capacitive gap. The conventional astable multivibrator shown in FIG. 2A results in a relatively slow rise rate as shown in FIG. 3A at the beginning of the $t_1$ pulse or in FIG. 3B at the beginning of the $t_2$ pulse. As a result, the ratio of $t_1$ to $t_2$ will be difficult to determine due to the indeterminate juncture between $t_1$ and $t_2$, evident most clearly in FIG. 3B. The low rise rate results in a variation in the detected interval.

Referring to FIG. 2B, one method of reducing this variation is illustrated. In addition to the conventional cross coupled first and second switching stagess Q1 and Q2 forming the multivibrator, a capacitor diode network is coupled to both points A and B to generate the sharply rising pulses shown in FIG. 3C. The characteristic shown in FIG. 3C represents the output pulse occurring at point C in the circuit each time the voltage at point A drops due to the turning on of transistor Q1, through the capacitor $C_3$, to the base of transistor Q3, due to the action of diodes $D_1/D_2$. A similar pulse occurs at point C each time the voltage at point B drops due to the turning on of transistor Q2, through the capacitor $C_4$, to the base of transistor Q3, due to the action of the diode $D_3/D_4$. The resulting waveform is shown in FIG. 3C. As is evident, the waveform of FIG. 3C consists of a pulse train with alternate long and short intervals, corresponding to $t_1$ and $t_2$, marked by sharply rising spikes, the ratio of the intervals being determined in accordance with the temperature coefficients set up by resistance $R_1$ and $R_2$ or by the capacitors $C_1$ and $C_2$ in the same manner as described in conjunction with FIG. 2A. This pulse train may be transmitted by connecting the point C to the output electrode for coupling with a receiver, and represents a suitable variable periodic pulse train.

It will be evident from the foregoing description that the ideal waveform will be a waveform having an output consisting only of the ratio intervals between $t_1$ and $t_2$, and having the fastest rise time possible for maximum capacitive coupling across the electrode gap. Referring now to FIG. 2C, a preferred circuit for generating a suitable waveform is illustrated. The circuit shown in FIG. 2C consists of dually cross-coupled transistor pairs. The cross-coupling of the on-off action of the transistors are such that $Q_1$ and $Q_4$ are on while $Q_2$ and $Q_3$ are off and vice versa. Utilization of this format results in appreciable reduction of the switching time as well as a reduction power consumption of the circuit. Resistors $R_1$ and $R_2$ or capacitors $C_1$ and $C_2$ may again be utilized to determine temperature ratios by means of distinct coefficients of temperature. Other arrangements possible will be described in further detail below. In operation, the resistors $R_3$ and $R_4$ perform a function similar to resistors $R_3$ and $R_4$ in FIG. 2A, that of biasing. In FIG. 2C, however, the resistors $R_3$ and $R_4$ are reduced in value and supplemented by the addition of resistor-capacitor-transistor networks $R_5 C_3 Q_3$ and $R_6 C_4 Q_4$. In operation, when the transistor $Q_2$ is turned on, the drop in voltage at a point B' turns off transistor $Q_1$ and simultaneously turns on transistor $Q_3$ through the action of capacitor $C_3$. The low effective resistance of $R_3$ and $Q_3$ results in a rapid rise in the voltage at point A'. The base current flow through resistor $R_5$ maintains the voltage at A' after the effect of capacitor $C_3$ diminishes. Similar action at point B' occurs when the transistor $Q_1$ is again turned on and transistor $Q_2$ is turned off. The action of capacitor $C_3$ when capacitor $Q_4$ is turned on results in cutting off transistor $Q_3$. The resulting high effective resistance of resistor $R_3$ and transistor $Q_3$ allows very little current flow through transistor $Q_1$ and hence the power consumption of the circuit is very low. As was stated hereinabove, low power consumption is an important and desirable feature in maintaining battery life, particularly when used in a continuous transmission mode in a remote location such as upon the body of a patient for transmission of temperature data. The complementary transistor pairs may be replaced with C/MOS inverters, with a resultant reduction in power-drain. In this instance, a higher supply voltage may be necessary.

As was previously stated, the ratio of the intervals between the switching of the transistors and the transducer is temperature dependent. By selecting capacitors $C_1$ and $C_2$ with small equal temperature coefficients, resistor $R_1$ with a negligible temperature coefficient and with resistor $R_2$ having a large negative temperature coefficient (such as a thermistor device) the interval $t_1$ will be nearly constant and the interval $t_2$ will decrease with temperature. The ratio of the pulse width of $t_1$ to pulse period $t_1 + t_2$ will thus increase with increasing temperature. In an environment such as the clinical thermometer, wherein only a limited variation is necessary, the ratio variation will be nearly linear to the temperature variation and will be used to indicate the temperature.

The output waveforms at points A' and B' are illustrated in FIGS. 3D and 3E, and clearly illustrate the maximum desirable characteristics of a transmitter device utilized in accordance with the invention.

It should be noted that although thermistors are discussed as the large negative temperature coefficient element for resistor $R_2$, it should be evident that the use of the multivibrator of FIG. 3C as the transducer for other types of variations should also be considered. Thus, for example, the thermistor utilized as the resistor $R_2$ may also be a strain gage resistor, thereby allowing strain gage measurements to be made in the same manner i.e. remote transducing transmission, and temperature measurement. The use of a strain gage resistance would have a distinct advantage over conventional strain gage monitoring, particularly of the rotating member of a machine, since the conventional use of electrical brushes have a tendency to introduce noise into a transmitted signal. It should be noted that temperature transducers may be used for other purposes than clinical, such as to monitor temperatures at various remote locations or on rotating equipment.

Figure 4A:
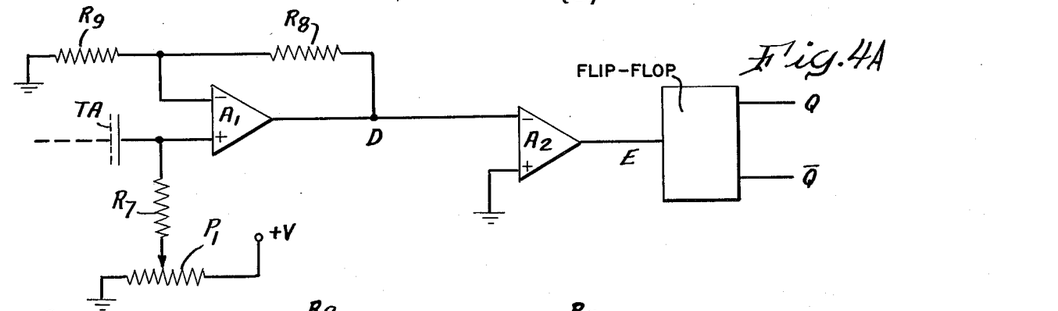
FIG. 4A and 4B illustrate preferred forms of receivers cooperating with the transmitter elements of FIG. 2.
Figure 4B:
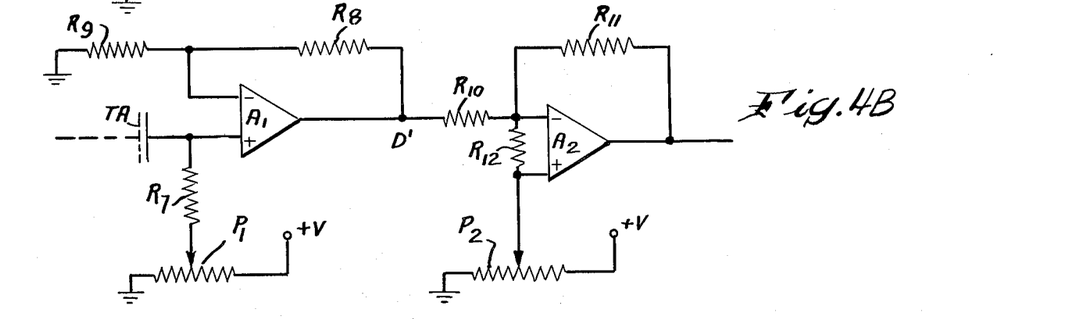

Referring now to FIGS. 4A and 4B, circuits for reproducing waveforms generated by the multivibrator of FIGS. 2B and 2C are shown. Referring to FIG. 4A, first and second operational amplifiers $A_1$ and $A_2$ are illustrated in a series connection, with the output of the operational amplifier $A_2$ connected to a flip-flop $FF_1$. The operational amplifier $A_1$ is a high gain amplifier having its noninverting input coupled to the transducer antenna TA. The potentiometer $P_1$ provides adjustable thresholding through a current limiting resistance $R_7$ to the noninverting input of the operational amplifier $A_1$. A feedback resistance $R_8$ is provided from the output of the amplifier $A_1$ to the inverting input of the amplifier $A_1$, and a further resistance $R_9$ couples the inverting input of the amplifier $A_1$ to a reference level. It will be evident that variations in the input signal through the capacitive electrode TA will be closely followed by the amplifier $A_1$ and thus the amplifier output of amplifier $A_1$ is closely related to the rate of rise and fall of the voltage at the transmitter antenna TA. Detected waveforms are illustrated in FIGS. 5A and 5D for FIGS. 4A and 4B respectively. The waveforms in FIG. 5A correspond to the transmission of a signal by the transmitter circuit shown in FIG. 2B, the waveform of which is shown in FIG. 3C. The amplifier $A_2$ in FIG. 4B is coupled as a feedback amplifier having an input resistor $R_{10}$, a feedback resistor $R_{11}$, a threshold resistor $R_{12}$, and a threshold adjusting potentiometer $P_2$. The waveform of FIG. 5D corresponds to the output E' of the amplifier in FIG. 4B illustrating receipt of a signal provided by the circuit of FIG. 2C, the waveform of which is shown in FIG. 3D.

The amplifier $A_2$ in FIG. 4A is a comparator, and is utilized to shape the pulses from the amplifier $A_1$ for satisfactory functioning as clock pulses in order to trigger the flip-flop circuit $FF_1$ for forming the square wave pulse train shown in FIG. 5B and in FIG. 5C, FIGS. 5B and 5C representing the outputs Q and $\overline{Q}$ of the flip-flop $FF_1$ of the FIG. 4A. It would be evident that since a ratio circuit is being employed, it is necessary to know which of the outputs Q or $\overline{Q}$ should be utilized for detection. A circuit for determining the appropriate output to be employed is illustrated in greater detail in FIG. 8, and will be discussed in conjunction with that figure.

Amplifier $A_2$ shown in FIG. 4B is also employed as a comparator and includes a feedback network connected to cause the state of the comparator to change only when the sharp rise or fall of the output of the amplifier $A_1$ occurs. The transducer output wave is thus reproduced at the output of the amplifier $A_2$ as shown in FIG. 5E. Thus, either the circuits of FIG. 4A or FIG. 4B may be employed in conjunction with its appropriate transmitter for generating a like output waveform, as shown in FIG. 5B or C, and in 5E.

The receiver unit may be desired to illustrate the data signal either in analog form as by means of a meter or in digital form as by means of a digital readout on a light emitting diode or liquid crystal display.

Figure 5:
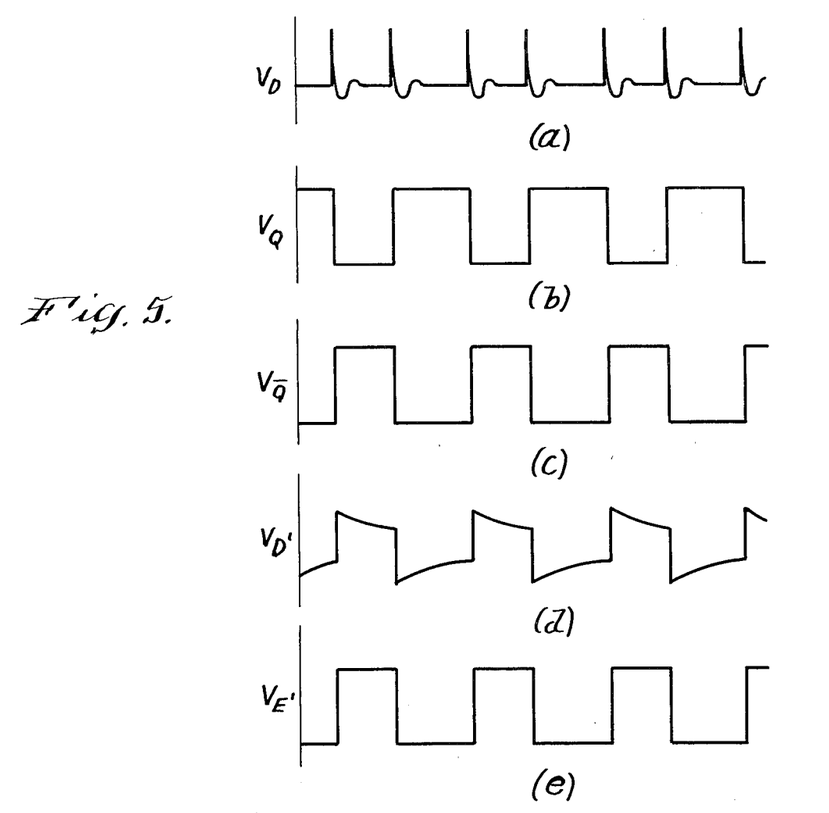
Figure 6:
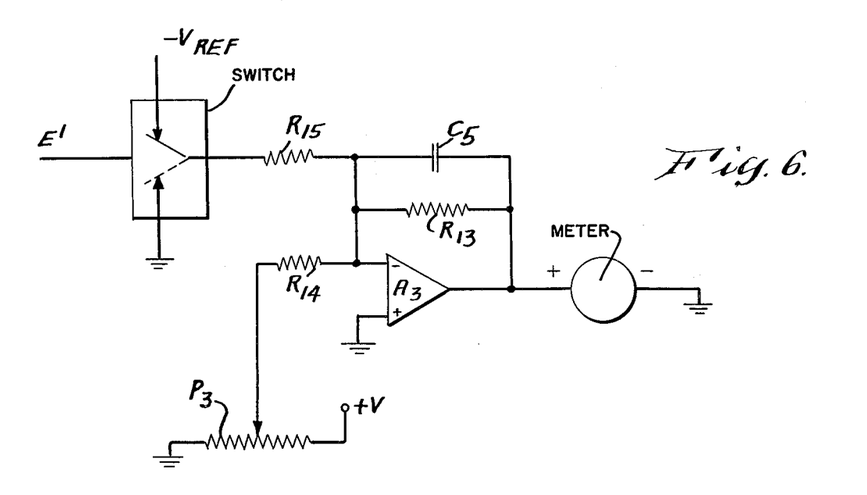
FIG. 6 is an analog meter display utilizable with the receivers of FIG. 4.

Referring more specifically to FIG. 5, there is illustrated the conversion of the transducer waveform of FIG. 3D as received by the receiving circuit of FIG. 4B into a voltage analog of the transduced parameter. The operational amplifier $A_3$ shown in FIg. 6 is provided with an exponential feedback network consisting of resistances $R_{13}$ and capacitor $C_5$, coupling the output of the amplifier $A_3$ to the inverting input of the amplifier $A_3$.

The input to the amplifier $A_3$ through the resistance $R_{15}$ is determined by the switching mechanism $S_1$ which provides for alternating the input line between a source of reference potential and ground, under the control of the voltage $E^1$. To this end, the switching mechanism $S_1$ may be a relay or solid state switch, or the like.

The output of amplifier $A_3$ will therefore exponentially increase while the -Vref potential is applied and exponentially decreases when the ground potential is applied. The resulting output voltage will therefore oscillate about a mean value which is proportional to the desired ratio $t_1/(t_1 + t_2)$.

Potentiometer $P_3$ and resistance $R_{14}$ provide means for offsetting the zero to permit selection of the low end of the scale as desired. The magnitude of the reference potential will thusly determine the range of the readings displayed on the meter.

In operation, the exponential feedback network consisting of $R_{13}$ and $C_5$ is provided with a long time constant when compared to the intervals $t_1$ and $t_2$ in order that the fluctuation in the output of the amplifier about the mean will be small. The output of the amplifier $A_3$ is therefore proportional to the desired ratio $t_1/(t_1 + t_2)$. The use of the offset adjustment indicated at potentiometer $P_3$ permits a measured range such as clinical temperature to be displayed on the milliammeter, adjusted to cover nearly the full scale of the instrument for maximum readability. Thus a very accurate analog display of the temperature variation may be produced.

The analog measurement may be replaced by a digital measurement at the output of the amplifier $A_3$ merely by replacing the milliameter with a digital voltmeter. In this case, it may be necessary to also include a filter for removing any ripple produced by the on-off action of the analog switch $S_1$.

Figure 7:
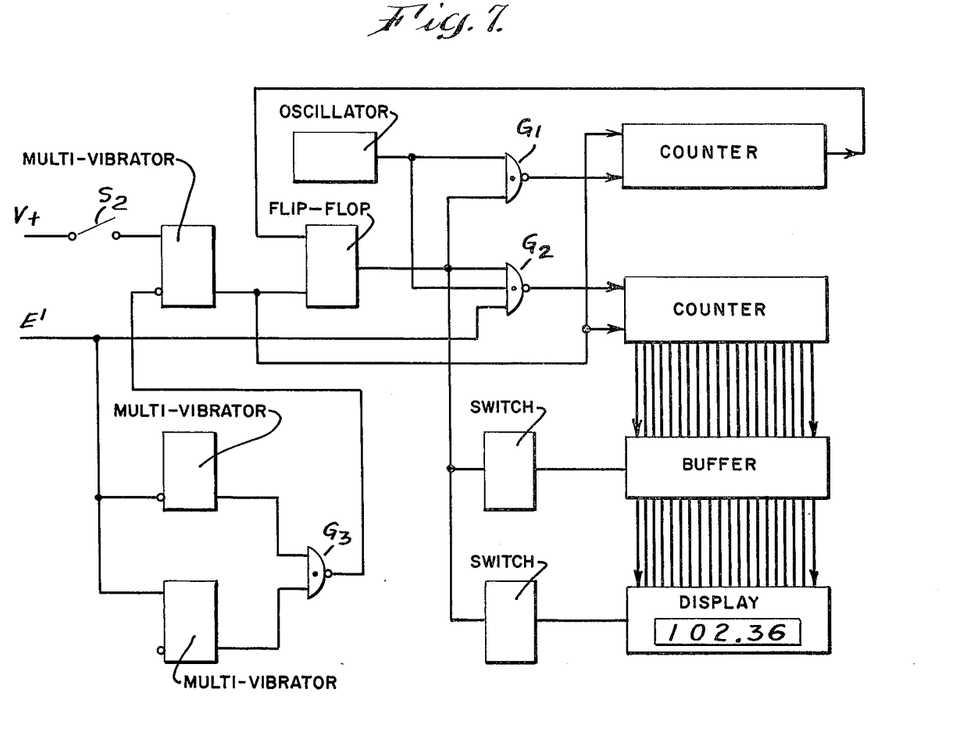
FIG. 7 is a digital output indicator utilizable with the receiver of FIG. 4B

Referring now to FIG. 7, a method of direct digital conversion of the output of a receiver is illustrated. This conversion is effected using the logic arrangement of FIG. 7 by initializing the operation through the switch $S_2$. Closing of the switch $S_2$ causes the one-shot multivibrator $OS_1$ to reset the counters $CN_1$ and $CN_2$ and thus set the flip-flop $FF_2$ for enabling the gates $G_1$ and $G_2$. The oscillator OSC generates a clock pulse string through gates $G_1$ and $G_2$ to counter $CN_1$ and $CN_2$. The clock pulse string will have a frequency larger than the frequency of the transducer. When the counter $CN_1$ overflows, the output of the counter $CN_1$ is coupled to the reset input of the flip-flop $FF_2$, thereby clearing the flip-flop $FF_2$. This will cease the operation of the counters $CN_1$ and $CN_2$ due to the inhibit now placed upon the gates $G_1$ and $G_2$. At this point, the counter $CN_2$ will contain a count proportional to the ratio $t_1/(t_1+t_2)$. By selecting the maximum count position of counter $CN_1$, the count at which overflow occurs, the count $CN_2$ will represent an appropriate number representation of the transduced measurement required. For example, if body temperature is being measured, the range of $CN_1$ and $CN_2$ will be set to vary, the $CN_2$ count, for example, between 95.00 and 110.00, representing degrees Farenheit. Obviously, Centigrade can also be employed and other ranges may be present in accordance with the desired parameters being transduced. The clearing of the flip-flop $FF_2$ initiates the transfer of the count from the counter $CN_2$ to a display buffer $DB_1$, activating the display DS. The display buffer $DB_1$ and display DS may be conventional in nature, such as integrated drive circuitry energizing a light emitting diode display, liquid crystal, display tubes, or the like, and activated through conventional switching circuits $S_3$ and $S_4$.

The one-shot multivibrator $OS_2$ is also activated each time the output of the receiver drops and $OS_3$ each time the voltage rises. Each one shot will have a negative output pulse having a duration approximately ¾ths of the period of the transducer wave. Since one or both of these outputs will be low as long as the transducer wave is received continuously, the output of gate $G_3$ will remain high. If, during the sampling period a receiver is not positioned to receive a continuous string of transducer pulses, gate $G_3$ will eventually enter a negative transition when the timer period of the one shots $OS_2$ and $OS_3$ is exceeded, thereby causing one shot $OS_1$ to re-initiate a conversion. Thus, this circuitry insures that valid readings are continuously displayed.

It is noted with regard to the analog configuration shown in FIG. 6 that no circuitry is necessary for insuring the validity of readings since absence of a signal will cause off scale readings and intermittent signals will cause eratic readings.

Figure 8:
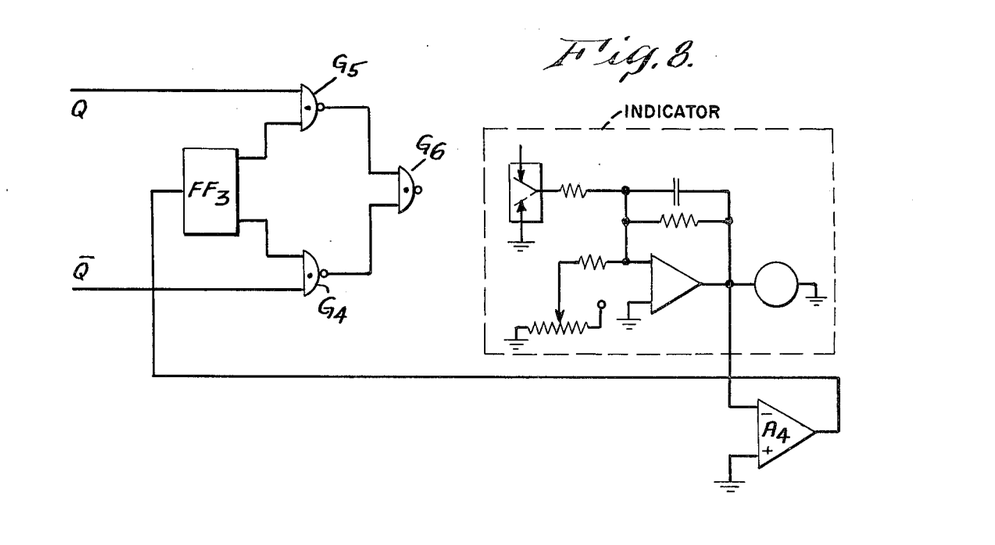
FIG. 8 shows an alternative form of circuitry necessary for obtaining a positive output in accordance with the use of the transmitter shown in FIG. 2B taken in conjunction with the receiver unit shown in FIG. 4A.

Referring to FIG. 8, a phase detecting circuit is utilized for obtaining a positive output when the transducer system of FIG. 2D is employed in the transmission is illustrated. Thus, when the inverted output of the flip-flop $FF_1$ shown in FIG. 4A is gated to the amplifier $A_3$, the output will be negative instead of positive. A negative output will be detected by a comparator amplifier $A_4$, which in turn will cause flip-flop $FF_3$ to change state, and thereby gate the correct receiver output into the amplifier $A_3$ for correcting the polarity of the signal. This is accomplished by gating the complemented output into the gate $G_4$ and the uncomplemented output into the gate $G_5$. Receipt by the analog unit shown in FIG. 6 of the incorrect polarity signal will be inverted in the amplifier $A_4$ and will thus select the gate $G_5$, permitting the non-complemented output of flip-flop $FF_1$ to pass through the gate $G_6$ for entrance into the analog display circuit of FIG. 6.

The transmitter circuits of FIG. 2 lend themselves particularly to calibration when constructed as an integrated circuit. Thus, when resistors are deposited, the transducer may be calibrated to produce a true reading at two points on its scale. This may be accomplished by screening the temperature sensitive resistance $R_2$ in two portions, a major portion $R_2'$ which will be pressure sensitive and a minor portion $R_2''$. The output at a selected point can be set by trimming the resistor on a 1. Obviously, other forms of calibrating by presetting the resistances $R_1$ and $R_2$ may be accomplished within the framework of the present invention.

The capacitive coupling of the transmitter and receiver electrodes may be accomplished by any conventional techniques. For example, the transmitter and receiver may each include a conductive plate or wire positioned in proximity to the outer surface of each unit. The coupling is thus achieved by bringing the respective electrode of a receiver into proximity with the electrode of a transmitter.

By way of illustration and with the intent to be exemplary and not in any way limiting, the circuit elements disclosed herein may employ the following parameters.

| | | |
|---|---|---|
| FIG. 2A - | | $C_1$... 75pf |
| | | $C_2$... 75pf |
| | | $R_1$... 150K |
| | | $R_2$... 150K |
| | | $R_3$... 27K |
| | | $R_4$... 27K |
| | | $Q_1$... 2N3640 |
| | | $Q_2$... 2N3640 |
| | | $V_1$... 1.5V |
| FIG. 2B - | | $V_1$... 1.5V |
| | | $R_1$... 150K |
| | | $R_2$... 150K |
| | | $R_3$... 27K |
| | | $R_4$... 27K |
| | | $C_1$... 75pf |
| | | $C_2$... 75pf |
| | | $C_3$... 75pf |
| | | $C_4$... 75pf |
| | | $Q_1$... 2N3640 |
| | | $Q_2$... 2N3640 |
| | | $D_1$... 7I-51 |
| FIG. 2C - | | $R_1$... 150K |
| | | $R_2$... 150K |
| | | $R_3$... 39Ω |
| | | $R_4$... 39Ω |
| | | $R_5$... 220K |
| | | $R_6$... 220K |
| | | $C_1$... 75pf |
| | | $C_2$... 75pf |
| | | $C_3$... 25pf |
| | | $C_4$... 25pf |
| | | $Q_1$... 2N3640 |
| | | $Q_2$... 2N3640 |
| | | $Q_3$... 2N3646 |
| | | $Q_4$... 2N3646 |
| FIG. 4A - | | $R_7$... 1M |
| | | $R_8$... 1M |
| | | $R_9$... 1K |
| | | $P_1$... 50K |
| FIG. 4D - | | $R_7$... 1M |

FIG. 6 -

-continued $R_8$... 1M
$R_9$... 1M
$R_{10}$... 100K
$R_{11}$... 100K
$R_{12}$... 20K
$P_2$... 50K
$R_{13}$... 500K
$R_{14}$... 100K
$R_{15}$... 100K
$P_3$... 20K
$C_5$... 1μf The amplifiers may be conventional differential amplifiers. Thus, $A_1A_1$, may be μ741, and $A_2A_2$, may be μ710, manufactured by the Fairchild Instrument Corporation.

It is emphasized that the transducing parameters to be transmitted and detected may include a variety of physical conditions, including temperature, strain, and other detectable quantities for which the present invention may find utility. Since certain other changes may be made in the foregoing disclosure without departing from the scope of the invention as herein involved, it is intended that all matter contained in the foregoing description and depicted in the accompanyiing drawings be construed in an illustrative and not a limiting sense.

What is claimed is:

1. A transducer system comprising a plurality of transmitters, each of said transmitters including means for generating an asymmetric wave form, the asymmetry of said wave being proportional to a quantity being transduced, each of said transmitters including a capacitive coupling output electrode, a receiver, said receiver including a capacitive coupling input electrode adapted to be selectively positioned closely adjacent and electrostatically coupled to any one of said transmitter electrodes to receive signals therefrom, said electrostatic coupling comprising the principal signal coupling between said transmitters and receiver, said receiver including means for converting said asymmetric wave to a representation of said transduced quantity in proportion to said asymmetry.

2. A transducer system comprising a plurality of transmitters, each of said transmitters including means for generating an asymmetric wave form, the asymmetry of said wave being proportional to a quantity being transduced, each of said transmitters including a capacitive coupling output electrode, a receiver, said receiver including a capacitive coupling input electrode adapted to be selectively positioned closely adjacent and electrostatically coupled to any one of said transmitter electrodes, said receiver including means for converting said asymmetric wave to a magnitude representation of said transduced quantity in proportion to said asymmetry, said transmitter including an asymmetric pulse generator comprising a first stage and a second stage, said first stage including first and second transistors, said second stage including first and second transistors, said first stage first and second transistors and said second stage first and second transistors each being coupled in series current relationship within each of said stages, means connecting the junction of said first stage first and second transistors to the respective inputs of said second stage first and second transistors, and means for coupling the junction of said second stage first and second transistors to the inputs of said first stage first and second transistors respectively, first means for determining the time constant of said first stage, and second means for determining the time constant of said second stage, said first and second time constants differing, and means for biasing said first and second stage such that said first stage first transistor and said second stage second transistor are on while the remaining transistors are off, and said first stage second transistor and said second stage first transistor are off while the other transistors are on, said first and second means establishing a transmission ratio indicative of said transduced quantity.

3. The system of claim 1 wherein said receiver includes a first amplifier and a second amplifier, said first amplifier comprising a high gain operational amplifier having said electrostatically coupled input electrode connected to one input thereof, and a signal fed back from the output thereof to the remaining input thereof, said amplifier following the rate of rise and fall of the signal transmitted by said transmitter, and a display means coupled to said first amplifier for displaying a magnitude proportional to said transduced quantity.

4. The combination of claim 3 wherein said display means includes a further amplifier, said amplifier including an exponential feedback network having a relatively long time constant compared to the asymmetric intervals of said transmitted signal, said further amplifier integrating said square wave pulses, said display means indicating said integrated level as an analog of said transmitted asymmetry.

5. The combination of claim 3 wherein said display means includes a first counter and a second counter, a source of clock pulses, means for gating input pulses from said transmitter and clock pulses to said first and second counters, means for establishing a predetermined count level in said first counter, a bistable means responsive to an overflow condition in said first counter, said bistable means disconnecting said source of input pulses from said first and second counters, switching means coupled to said bistable means, display means coupled to said second counter, said switching means responsive to said bistable means disconnecting said first and second counter for enabling said display means and displaying the contents of said second counter.

6. An asymmetric pulse generator comprising a first stage and a second stage, said first stage including first and second transistors, said second stage including first and second transistors, said first stage first and second transistors and said second stage first and second transistors each being coupled in series current relationship within each of said stages, means connecting the junction of said first stage first and second transistors to the respective inputs of said second stage first and second transistors, and means for coupling the junction of said second stage first and second transistors to the inputs of said first stage first and second transistors respectively, first means for determining the time constant of said first stage, second means for determining the time constant of said second stage, said first and second time constants differing, and means for biasing said first and second stage such that said first stage first transistor and said second stage second transistor are on while the remaining transistors are off, and said first stage second transistor and said second stage first transistor are off while the other transistors are on, said first and second means establishing an asymmetry indicative of a transduced quantity, and further comprising a receiver electrostatically selectively manually coupled to said generator, said receiver comprising first and second series coupled amplifiers, a capacitive coupling input electrode, said first amplifier comprising a high gain operational amplifier having said input electrode connected to one input thereof, and a signal fed back from the output thereof to the remaining input thereof, said amplifier following the rate of rise and fall of the signal transmitted by said transmitter, and a display means coupled to said second amplifier for displaying a magnitude proportional to said transduced quantity.

7. The combination of claim 6 wherein said display means includes a further amplifier, said amplifier including an exponential feedback network having a relatively long time constant compared to the asymmetric intervals of said transmitted signal, said further amplifier integrating said square wave pulses, said display means indicating said integrated level as an analog of said transmitted asymmetry.

8. The combination of claim 6 wherein said display means includes a first counter and a second counter, a source of clock pulses, means for gating input pulses from said transmitter and clock pulses to said first and second counters, means for establishing a predetermined count level in said first counter, a bistable means responsive to an overflow condition in said first counter, said bistable means disconnecting said source of input pulses from said first and second counters, switching means coupled to said bistable means, display means coupled to said second counter, said switching means responsive to said bistable means disconnecting said first and second counter for enabling said display means and displaying the contents of said second counter.

9. A transducer system comprising a plurality of transmitters, each of said transmitters including means for generating a variable periodic pulse train, the variable periodicity of said pulse train being proportional to a quantity being transduced, each of said transmitters including a capacitive coupling output electrode, a receiver, said receiver including a capacitive coupling input electrode adapted to be selectively positioned closely adjacent and electrostatically coupled to any one of said transmitter electrodes for receiving signals therefrom, whereby said electrostatic coupling comprises the principal signal coupling between said transmitters and receiver, said receiver including means for converting said variable periodic pulse train to a representation of said transduced quantity in proportion to said variable periodicity.

10. A transducer system comprising a plurality of transmitters, each of said transmitters including means for generating a variable periodic pulse train, the variable periodicity of said pulse train being proportional to a quantity being transduced, each of said transmitters including a capacitive coupling output electrode, a receiver, said receiver including a capacitive coupling input electrode adapted to be electrostatically coupled direction, to any one of said transmitter electrodes, said receiver including means for convering said variable periodic pulse train to a magnitude representation of said transduced quantity in proportion to said variable periodicity, said transmitter including a variable periodic pulse generator comprising a first switching stage and a second switching stage, means cross coupling said first and second stages in a free running multivibrator configuration, a third stage, first coupling means coupling said first stage to said third stage for producing a sharply rising signal at a point in said third stage when said first stage is switched in a first current direction, second coupling means coupling said second stage to said third stage for providing a sharply rising signal at said point in said third stage when said second stage is switched in said first current direction, and a capacitive coupling output electrode coupled to said point in said third stage, first means controlling the time constant of said first stage, second means controlling the time constant of said second stage, said first and second time constants differing, said first and second means thereby establishing a variable periodic transmission ratio indicative of said transduced quantity.

11. The system of claim 10 wherein each said coupling means includes a capacitor and first diode series coupled between the respective stages, and a second diode coupling the junction of said capacitor and diode to a reference level.

12. The system of claim 10 wherein said receiver includes a first amplifier and a second amplifier, said first amplifier comprising a high gain operational amplifier with first and second inputs and having a capacitive coupling input electrode connected to said first input, and a signal fed back from the output thereof to said second input, said amplifier following the rate of rise and fall of the voltage transmitted by said transmitter, and a display means coupled to said first amplifier for displaying a magnitidue proportional to said transduced quantity.

13. The system of claim 12 wherein said second amplifier includes a bistable output means triggered into respective bistable conditions by said sharply rising signals, and said display means includes a phase detection circuit for gating the correct polarity signal to said display means.

14. The system of claim 13 wherein said display means includes a further amplifier, said amplifier including an exponential feedback network having a relatively long time constant compared to the variable periodic intervals of said transmitted signal, said further amplifier integrating said square wave pulses, said display means indicating said integrated level as an analog of said transmitted aperiodicity.

15. The system of claim 13 wherein said display means includes a first counter and a second counter, a source of clock pulses, means for gating input pulses from said transmitter and clock pulses to said first and second counters, means for establishing a predetermined count level in said first counter, a bistable means responsive to an overflow condition in said first counter, said bistable means disconnecting said source of input pulses from said first and second counters, switching means coupled to said bistable means, display means coupled to said counter, said switching means responsive to said bistable means disconnecting said first and second counter for enabling said display means and displaying the contents of said second counter.

16. A variable periodic pulse generator comprising a first switching stage and a second switching stage, means cross coupling said first and second stages in a free running multivibrator configuration, a third stage, first coupling means coupling said first stage to said third stage for producing a sharply rising signal at a point in said third stage when said first stage is switched in a first current direction, second coupling means coupling said second stage to said third stage for providing a sharply rising signal at said point in said third stage when said second stage is switched in said first current direction, and a capacitive coupling output electrode coupled to said point in said third stage, first means controlling the time constant of said first stage, second means controlling the time constant of said second stage, said first and second time constants differing, said first and second means thereby establishing a variable periodic transmission ratio indicative of a transduced quantity, further including a receiver, said receiver including a first amplifier and a second amplifier, said first amplifier comprising a high gain operational amplifier with first and second inputs having a manually positionable capacitive coupling input electrode coupled to said output electrode and connected to said first input, and a signal fed back from the output thereof to the second input, said amplifier following the rate of rise and fall of the voltage transmitted by said transmitter, and a display means coupled to said first amplifier for displaying a magnitude proportional to said transduced quantity.

17. The generator of claim 16 wherein said second amplifier includes a bistable output means triggered into respective bistable conditions by said sharply rising signals, and said display means includes a phase detection circuit for gating the correct polarity signal to said display means.

18. The generator of claim 17 wherein said display means includes a further amplifier, said amplifier including an exponential feedback network having a relatively long time constant compared to the variable periodic intervals of said transmitted signal, said further amplifier integrating said square wave pulses, said display means indicating said integrated level as an analog of said transmitted variable periodicity.

19. The generator of claim 17 wherein said display means includes a first counter and a second counter, a source of clock pulses, means for gating input pulses from said transmitter and clock pulses to said first and second counters, means for establishing a predetermined count level in said first counter, a bistable means responsive to an overflow condition in said first counter, said bistable means disconnecting said source of input pulses from said first and second counters, switching means coupled to said bistable means, display means coupled to said counter, said switching means responsive to said bistable means disconnecting said first and second counter for enabling said display means and displaying the contents of said second counter.

20. A monitoring system comprising at least one transmitter, said transmitter including means for generating a repetitive pulse waveform, said pulse waveform having a characteristic which varies in proportion to a quantity being sensed, each of said transmitters including electrode means adapted to transmit said signal waveforms at a predetermined signal strength, a receiver, said receiver having mobility with respect to said transmitter and including electrode means adapted to be selectively positioned closely adjacent and capacitively coupled to said transmitter electrode means when moved into proximity thereto, the capacitive coupling between electrodes comprising the principal signal coupling between said tranmitter and receiver, thereby allowing said receiver to detect said signal waveform, said receiver including means for converting said detected signal waveform to a representation of said quantity in proportion to said characteristics.

21. The system of claim 20 wherein said system includes a plurality of transmitters, each responsive to a sensed quantity.

22. The system of claim 21 wherein said plurality of transmitters are each spaced one from the other so as to be relatively non-interferring.

* * * * *

UNITED STATES PATENT AND TRADEMARK OFFICE
CERTIFICATE OF CORRECTION

PATENT NO. : 3,940,752
DATED : February 24, 1976
INVENTOR(S) : Willard E. Bair

It is certified that error appears in the above-identified patent and that said Letters Patent are hereby corrected as shown below:

IN THE ABSTRACT, line 8, after "including" insert --a--.

Column 11, line 57, delete "direction,".

Signed and Sealed this

Twenty-sixth Day of October 1976

[SEAL]

Attest:

RUTH C. MASON
*Attesting Officer*

C. MARSHALL DANN
*Commissioner of Patents and Trademarks*